United States Patent
Onishi et al.

(10) Patent No.: US 7,982,451 B2
(45) Date of Patent: Jul. 19, 2011

(54) SENSING INSTRUMENT

(75) Inventors: Naoki Onishi, Sayama (JP); Hiroyuki Kukita, Sayama (JP); Shunichi Wakamatsu, Sayama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 261 days.

(21) Appl. No.: 12/311,261

(22) PCT Filed: Sep. 27, 2007

(86) PCT No.: PCT/JP2007/069402
§ 371 (c)(1),
(2), (4) Date: Jun. 10, 2009

(87) PCT Pub. No.: WO2008/038829
PCT Pub. Date: Apr. 3, 2008

(65) Prior Publication Data
US 2009/0273335 A1  Nov. 5, 2009

(30) Foreign Application Priority Data

Sep. 29, 2006 (JP) .................................. 2006-269226

(51) Int. Cl.
G01N 27/00 (2006.01)
G01R 23/14 (2006.01)
(52) U.S. Cl. .................. 324/71.1; 324/76.41; 324/76.45
(58) Field of Classification Search .......................... None
See application file for complete search history.

(56) References Cited

U.S. PATENT DOCUMENTS

| 7,555,952 | B2 * | 7/2009 | Onishi et al. ................... 73/579 |
| 7,598,723 | B2 * | 10/2009 | Gaillard et al. ............ 324/76.42 |
| 2008/0156097 | A1 | 7/2008 | Onishi et al. | |

FOREIGN PATENT DOCUMENTS

| JP | 6-241972 | 9/1994 |
| JP | 2001-083154 | 3/2001 |
| JP | 2001-304945 | 10/2001 |
| JP | 2006-184260 | 7/2006 |

* cited by examiner

Primary Examiner — Minh N Tang
(74) Attorney, Agent, or Firm — Jordan and Hamburg LLP

(57) ABSTRACT

In adopting a structure in which an oscillator circuit unit and an instrument main body including a measuring unit are separately formed in a sensing instrument measuring the concentration of or determining the presence/absence of a substance to be sensed by using a quartz sensor, the present invention has an object to enable the instrument main body side to know an oscillation frequency of the connected oscillator circuit unit. A plurality of band-pass filters having pass characteristics corresponding to oscillation frequencies of the oscillator circuits respectively are provided in the instrument main body side to sort frequency signals, it is determined whether or not levels of the sorted frequency signals are equal to or higher than a threshold value, and a switching unit is controlled so as to connect a channel having a signal level equal to or higher than the threshold value to the measuring unit, and a reference frequency used in the measuring unit, for instance, is selected according to the frequency of the frequency signal corresponding to this channel.

6 Claims, 9 Drawing Sheets

SENSING INSTRUMENT

TECHNICAL FIELD

The present invention relates to a sensing instrument which uses a sensing sensor including a piezoelectric resonator changing in natural frequency by the adsorption of a sample and which senses the adsorption of the sample based on the change in the natural frequency of the piezoelectric resonator.

BACKGROUND ART

As a method for sensing a trace substance, a sensing instrument using a quartz resonator has been known. This sensing instrument has a quartz sensor in which an adsorption layer for adsorbing a substance to be sensed is formed on a front surface of the quartz resonator, and measures the presence/absence or concentration of the substance to be sensed by utilizing the fact that when the substance to be sensed is adsorbed by the quartz resonator, more particularly, the adsorption layer, its natural frequency changes according to an adsorption amount of the substance to be sensed, and this sensing instrument is advantageous in that it is applicable to a wide range and has a simple structure as an instrument, and moreover, is capable of measuring even an extremely minute amount of substance because of its high sensitivity. For example, a patent document 1 describes that the use of a quartz sensor in the analysis of a disease marker substance contained in blood, urine, and the like is an effective method alternative to an immuno-latex kit which requires an expensive, large autoanalyzer.

The present inventor has been studying the possibility of applying a quartz sensor to, for example, dioxin and PCB which are environmental pollutants, a disease marker in blood, or the like, and the achievement in high-precision measurement of a target substance by this method would be innovative. The reason is because a method using a gas-chromatography mass spectrometer and an ELISA method (enzyme-linked immunosorbent assay method), which are currently known as methods of measuring, for example, dioxin, have the following problems. The former requires an extremely high instrument cost and thus a considerably high analysis cost, and takes a long period of time for analysis, and the latter is low in analysis precision, though requiring less instrument cost and analysis cost and taking a shorter period of time for analysis compared with the gas-chromatography mass analyzer.

A major part of a sensing instrument using a quartz resonator is structured such that an adsorption layer adsorbing a substance to be sensed, which has, for example, an antibody causing an antibody-antigen reaction is formed on the quartz resonator, an oscillator circuit is connected to the quartz resonator, and a frequency measuring unit measuring an oscillation frequency of the oscillator circuit is provided. After experiments on various kinds of substances to be sensed were repeated in order to determine an appropriate range of the oscillation frequency of the quartz resonator, it has been found out that even a frequency range appropriate for some kind of substance to be sensed is not sometimes appropriate for another substance to be sensed, and therefore, instead of fixing the oscillation frequency of the quartz resonator to one frequency, an actual product is preferably structured to be capable of selecting the oscillation frequency from a plurality of oscillation frequencies, for example, from at least two oscillation frequencies.

Further, a patent document 2 describes that, instead of measuring the oscillation frequency of a quartz resonator itself, calculating its difference from a reference frequency to measure a frequency change in the difference frequency is an advantageous method of measuring the frequency because a far lower frequency than the oscillation frequency is a target of this measurement. The patent document 2 further describes a structure in which sensor resonators different in oscillation frequency are used, differences between the oscillation frequencies fr1 to frn of the respective sensor resonators and reference frequencies f1 to fn corresponding to the oscillation frequencies fr1 to frn respectively are detected by a sampling circuit, and the detected difference of a channel selected by a selector is taken into a calculating device Depending on the application of the sensing instrument of this type, it is sometimes preferable to separate an oscillator circuit-side unit to which the quartz sensor is inserted and an instrument main body including a measuring system and make them attachable/detachable to/from each other via a cable. However, in such an instrument, it is difficult to adopt the measuring method using the differences between the oscillation frequencies and the reference frequencies. The reason is that the reference frequency has to be selected according to the oscillation frequency of the used quartz sensor, but the oscillation frequencies are assigned individually to the respective oscillator circuit units, and in an instrument in which the oscillation frequency is changed by the replacement of the oscillator circuit unit, the instrument main body side does not know which of the oscillation frequencies is used. Such a problem is overcome if the oscillator circuit units and the instrument main bodies are in one-to-one correspondence, but this cannot be said to be a realistic product in view of cost and space.

Patent document 1
Japanese Patent Application Laid-open No. 2001-83154: paragraphs 0002, 0004
Patent document 2
Japanese Patent Application Laid-open No. Hei 6-241972

DISCLOSURE OF THE INVENTION

The present invention was made under such circumstances, and has an object to provide a sensing instrument using a piezoelectric resonator such as a quartz resonator whose natural frequency changes by the adsorption of a sample, wherein an oscillator circuit unit and an instrument main body including a measuring unit are separately formed and the oscillation frequency is changeable by the replacement of the oscillator circuit unit.

The present invention is a sensing instrument which uses a sensing sensor including a piezoelectric resonator changing in natural frequency by the adsorption of a sample and which senses the adsorption of the sample based on the change in the natural frequency of the piezoelectric resonator, the instrument including:

an oscillator circuit unit to which the sensing sensor is connected and which includes an oscillator circuit for oscillating the piezoelectric resonator of the sensing sensor;

an instrument main body attachably/detachably connected to the oscillator circuit unit and including a measuring unit measuring a signal regarding a frequency of an oscillation output of the oscillator circuit;

a frequency sorting circuit provided in the instrument main body, and including a plurality of channels and a plurality of band-pass filters, the channels branching off from a frequency signal line extending from the oscillator circuit unit, and the band-pass filters being provided in the channels respectively and having pass characteristics corresponding to the oscillation frequencies of the oscillator circuits respectively;

a switching unit connecting a selected channel among the plural channels to the measuring unit;

a plurality of level detecting circuits detecting signal levels at output sides of the plural band-pass filters respectively; and a control unit comparing level detection values, which are detected by the plural level detecting circuits respectively, with a threshold value, controlling the switching unit so as to connect, to the measuring unit, a channel for which the level detection value equal to or higher than the threshold value is output, and controlling the measuring unit according to a frequency of a frequency signal corresponding to the connected channel.

The measuring unit measures the signal regarding the frequency of the oscillation output of the oscillator circuit, and "the signal regarding the frequency" refers to, for example, the frequency or the signal level of the frequency signal.

The piezoelectric resonator includes: an electrode provided on a front surface of a piezoelectric piece; and an adsorption layer formed on a front surface of the electrode to adsorb a substance to be sensed, and changes in the natural frequency when the substance to be sensed is adsorbed.

The following forms are adoptable in the present invention, for instance.

A. The measuring unit extracts a difference between a reference frequency selected from a plurality of reference frequencies and the frequency of the frequency signal from the oscillator circuit and measures a signal regarding the frequency corresponding to the difference, and the control unit selects the reference frequency from the plural reference frequencies according to the frequency of the frequency signal corresponding to the channel for which the level detection value equal to or higher than the threshold value is output.

B. At the time of the detection of the signal levels at the output sides of the band-pass filters, the control unit controls the switching unit so as to connect the channel whose signal level is to be detected to the measuring unit.

C. The oscillator circuit unit and the instrument main body are attachably/detachably connected via a cable, for example, a coaxial cable.

D. A feed line feeding a direct-current voltage to the frequency signal line on an input side of the frequency sorting circuit is connected to the instrument main body, a power supply line for taking out the direct-current voltage to an output side of the oscillator circuit is connected to the oscillator circuit unit, low-pass filters blocking passage of the oscillation output are provided in the feed line and the power supply line respectively, high-pass filters blocking passage of the direct-current voltage are provided between a connection point of the feed line and the band-pass filters in the frequency signal line, and between a connection point of the power supply line and the oscillator circuit in the frequency signal line respectively, and the direct-current voltage of the instrument main body side is supplied to the oscillator circuit side via the frequency signal line.

According to the present invention, in the sensing instrument using the piezoelectric resonator, for example, the quartz resonator whose natural frequency changes by the adsorption of the sample, the structure in which the oscillator circuit unit and the instrument main body including the measuring unit are separately formed is adopted, and in this structure, the plural band-pass filters having the pass characteristics corresponding to the oscillation frequencies of the oscillator circuits respectively are provided in the instrument main body side to sort the frequency signals, and the levels of the sorted frequency signals are detected. Therefore, it is possible to specify a channel (band-pass filter) having the signal level equal to or higher than the threshold value, based on the detection value of the signal level, and thus to know the oscillation frequency. As a result, it is possible to control the switching unit so as to connect this specified channel to the measuring unit, to control the measuring unit according to the frequency of the frequency signal corresponding to this channel, and to select the reference frequency corresponding to the oscillation output when, for example, a difference frequency between the frequency signal and the reference frequency signal is extracted and the signal regarding the frequency (for example, frequency or phase) is measured.

BEST MODE FOR CARRYING OUT THE INVENTION

Figure 1:
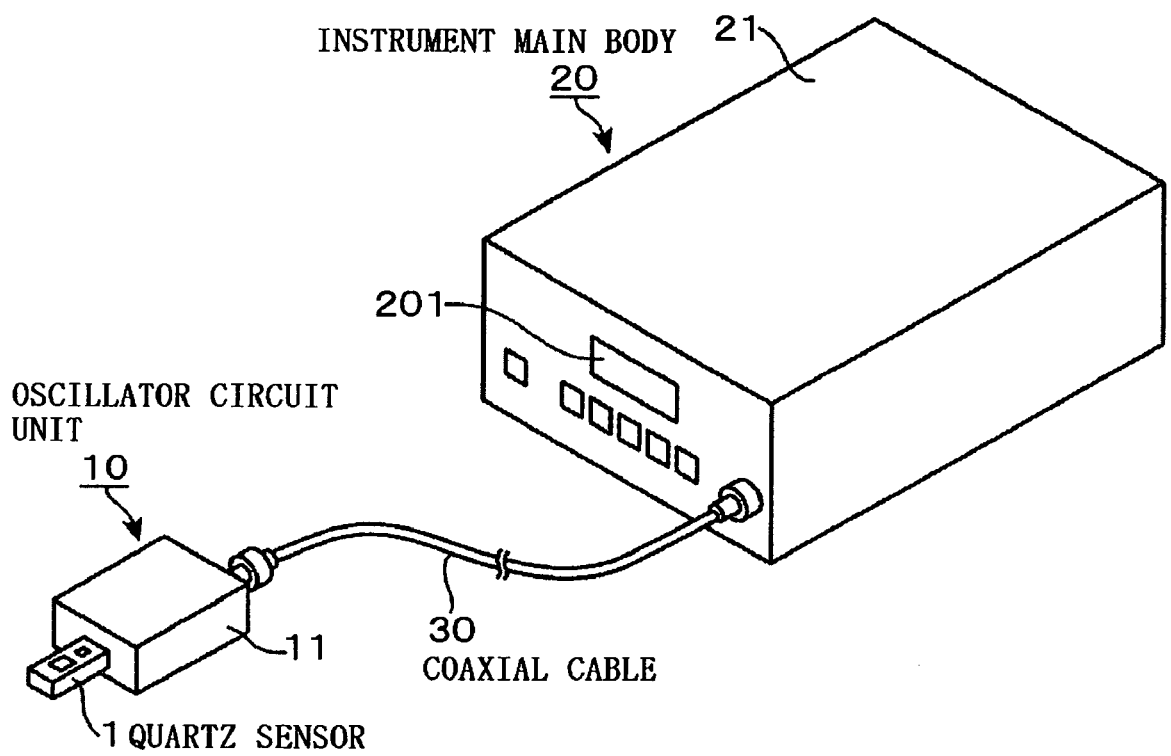
FIG. 1 is a perspective view showing an outer appearance of an embodiment of a sensing instrument according to the present invention.
Figure 3:
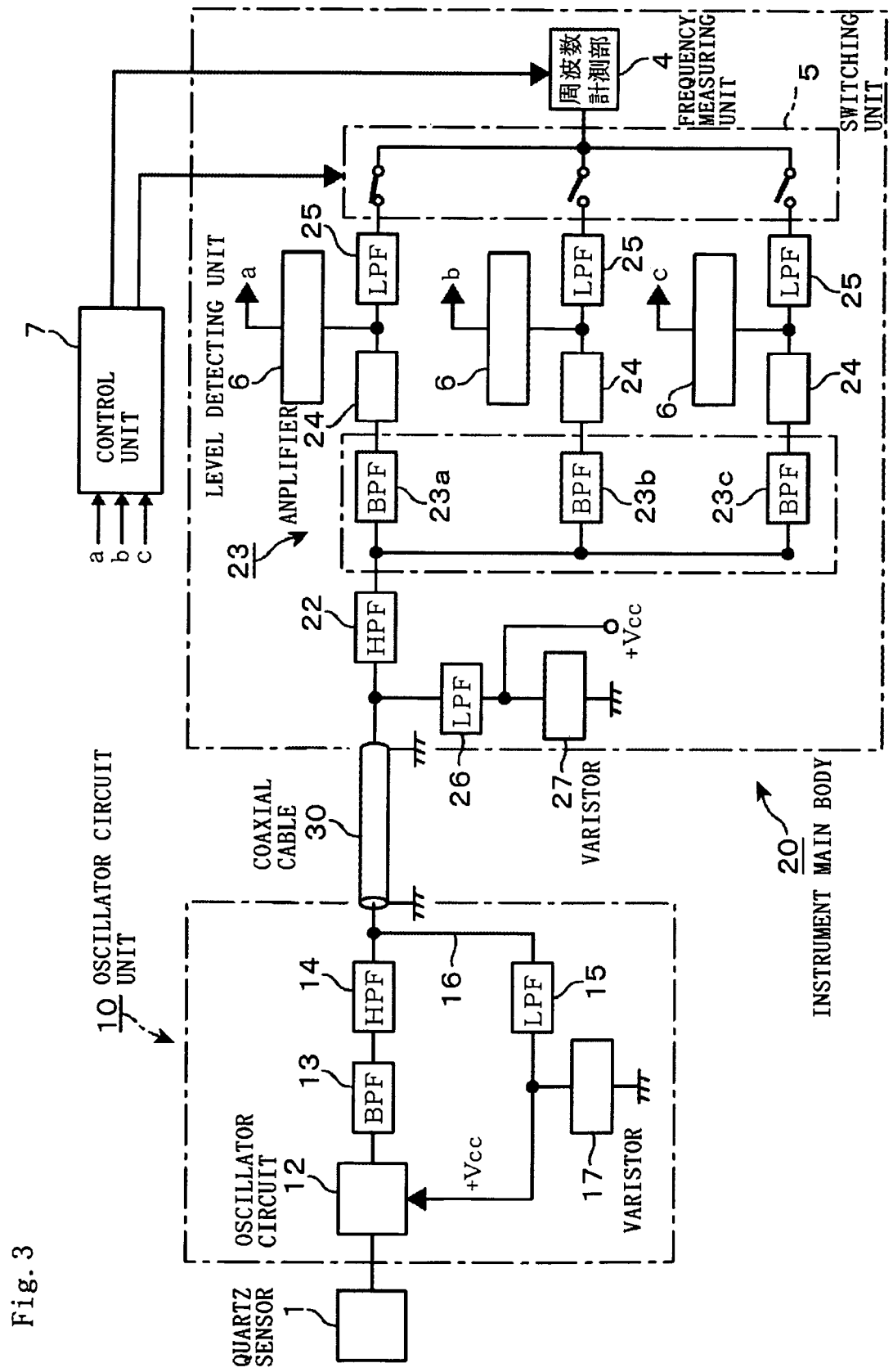
FIG. 3 is a block circuit diagram showing the whole circuit configuration of the embodiment.

Hereinafter, an embodiment of a sensing instrument according to the present invention will be described. As shown in FIG. 1 and FIG. 3, the sensing instrument includes an oscillator circuit unit 10 and an instrument main body 20, and the oscillator circuit unit 10 can be attachably/detachably connected to the instrument main body 20 by a cable, for example, a coaxial cable 30.

The oscillator circuit unit 10 has in its casing 11 an oscillator circuit 12, a band-pass filter (band filter) 13 which allows the passage of a signal with a resonance frequency of the oscillator circuit 12 (a main oscillation frequency of a later-described quarts resonator), and a high-pass filter 14.

Figure 2:
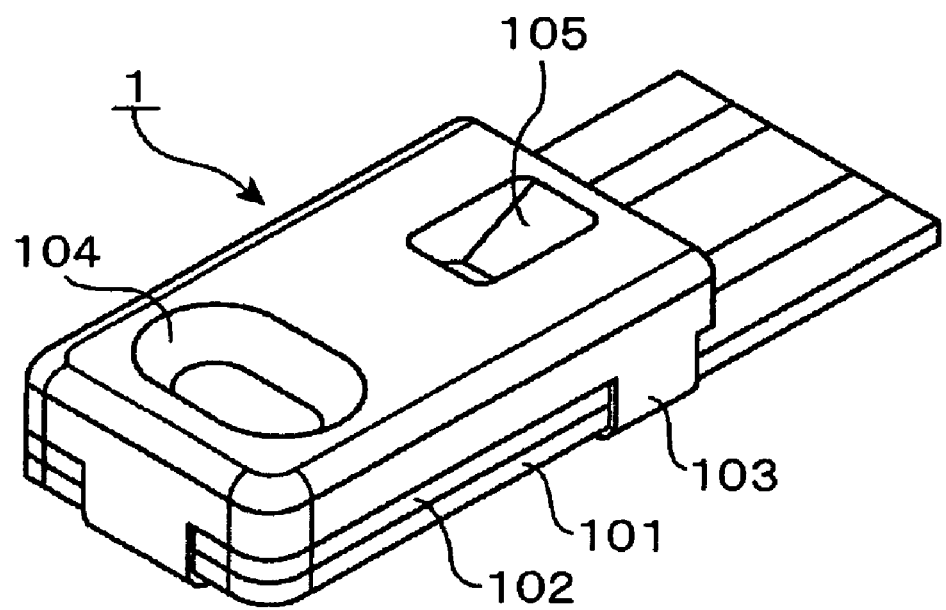
FIG. 2 is a perspective view of a quartz sensor used in the embodiment.

Further, a quartz sensor 1 which is a sensing sensor is attachably/detachably connected to the oscillator circuit unit 10. Since the quartz sensor 1 is generally known, only an example of its outer appearance is shown in FIG. 2, and the quartz sensor 1 is structured such that a rubber sheet 102 is stacked on a printed circuit board 101 as a wiring board whose one end is a connection terminal, a quartz resonator as a piezoelectric resonator is provided to cover a recessed portion provided in the rubber sheet 22, and an upper cover case 103 is mounted from an upper side of the rubber sheet 102. In the upper cover case 103, an injection port 104 for sample solution and a check port 105 for sample solution are formed, and the sample solution is injected from the injection port 104 to fill an upper surface-side space of the quartz resonator. The recessed portion on a lower surface side of the quartz resonator is an airtight space, whereby the quartz sensor of a Languban type is formed.

In the quartz resonator, excitation electrodes are formed on both surfaces of its quartz piece, and an adsorption layer for adsorbing a substance to be sensed is formed on a front surface of the excitation electrode. In a case where the substance to be sensed is, for example, an antigen such as protein, an antibody for capturing the antigen by an antigen-antibody reaction is used as the adsorption layer.

A circuit of the instrument main body 20 is housed in the casing 21 on whose front surface a display unit 201 and so on are provided, the display unit 201 displaying the result of measurement, for example, a frequency, a variation in the frequency, or the like by, for example, display characters of LED. In the circuit, a high-pass filter 22 and a frequency sorting circuit 23 in which a plurality of, for example, three band-pass filters (band filters) 23a to 23c for sorting frequencies are connected in parallel are provided along a signal line of a frequency signal from the oscillator circuit 12, and a series circuit of an amplifier 24 and a low-pass filter 25 is connected to each of output sides of the band-pass filters 23a to 23c. Three signal lines branching off at the frequency sorting circuit 23 from the signal line are called channels, and there is further provided a switching unit 5 selectively connecting downstream ends of the channels (output ends of the low-pass filters 25) to a frequency measuring unit 4 as a measuring unit.

The band-pass filters 23a to 23c are intended to selectively allow the passage of signals with frequencies corresponding to oscillation frequencies of the used oscillator circuit units 10, and if, for example, three 9 MHz, 30 MHz, and 60 MHz oscillator circuits are selected for use as the oscillator circuit units 10, band-pass filters corresponding to these frequencies are prepared.

Here, a power source of the instrument main body 20 and the oscillator circuit unit 10 will be described. A direct-current voltage+Vcc supplied to the circuit in the oscillator circuit unit 10 is connected to the signal line on an input side of the high-pass filter 22 via a low-pass filter 26. In the oscillator circuit unit 10, a power supply line 16 in which a low-pass filter 15 is inserted branches off from the signal line on an output side of a high-pass filter 14. 17, 27 denote varistors. With such a structure, the direct-current voltage on the instrument main body 20 side is superimposed on the signal line to be sent via a core wire of the coaxial cable 30 into the oscillator circuit unit 10, and the direct-current voltage+Vcc is not sent to the oscillator circuit 12 side via the high-pass filter 14 but is obtained through the low-pass filter 15. Therefore, in the oscillator circuit unit 10, the direct-current voltage+Vcc can be supplied to the oscillator circuit 12 and so on, and thus a direct-current power source need not be mounted, leading to a simple structure. An outer conductor of the coaxial cable 30 is grounded in the oscillator circuit unit 10 and the instrument main body 20.

Figure 4:
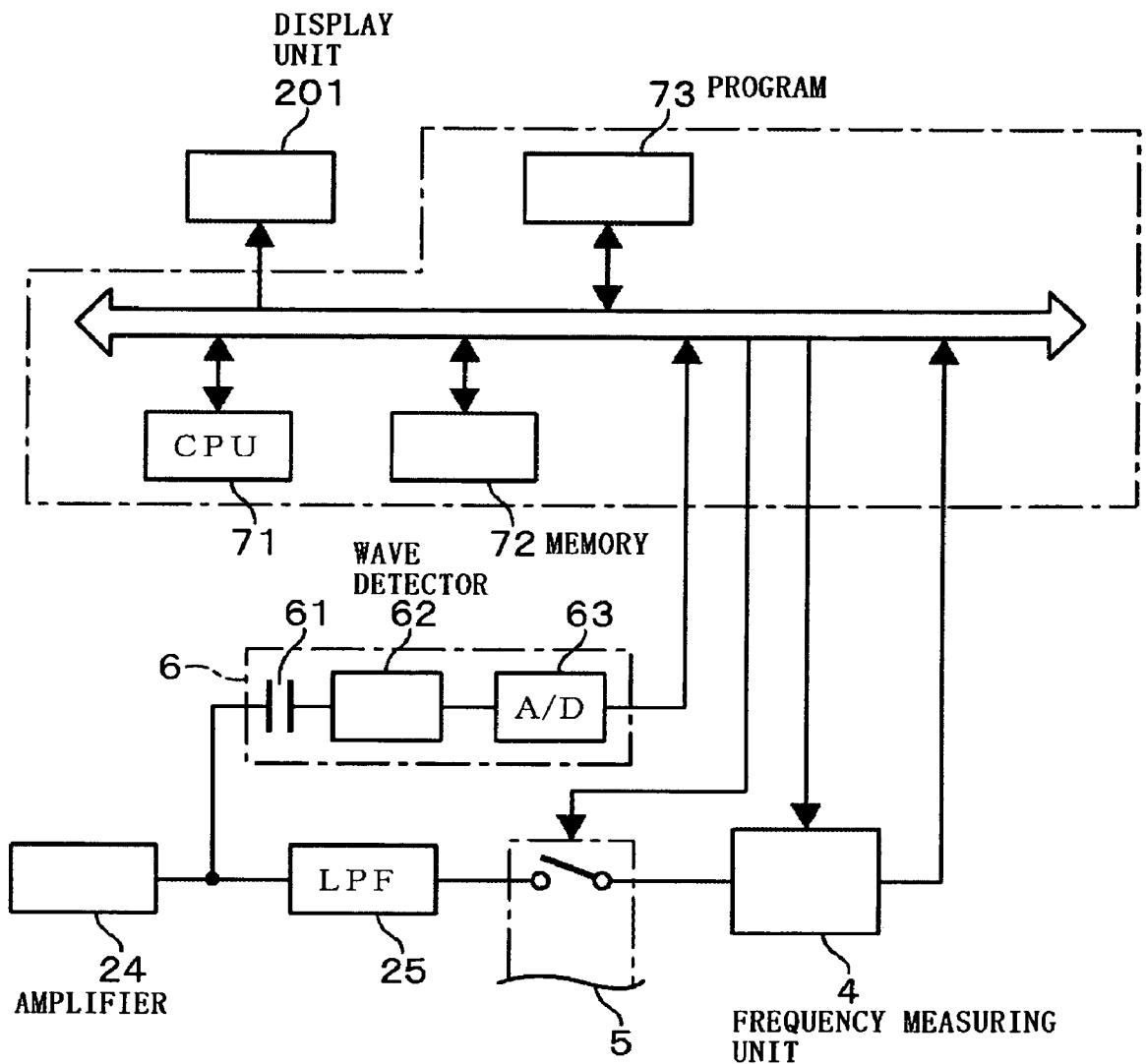
FIG. 4 is a block diagram showing a level detecting circuit and a control unit.

Further, in the instrument main body 20, level detecting units 6 are provided to detect signal levels (amplitudes) at output sides of the amplifiers 24 of the aforesaid channels respectively. As shown in FIG. 4, the level detecting units 6 each include a capacitor 61 for cutting a direct current of the amplifier 24, a wave detector 62, and an analog/digital (A/D) converter 63, and the signal levels detected here are input to a control unit 7 formed by a computer.

The control unit 7 includes a CPU 71, a work memory 72, and a program 73 for executing a series of processing necessary for the frequency measurement. Actually, the program 73 is stored in a ROM but is illustrated in a simplified manner. The program includes steps of sequentially connecting the three channels to the frequency measuring unit 4, comparing a level detection value of the connected channel with a threshold value, controlling the switching unit 5 so that the switching unit 5 connects this channel to the frequency measuring unit 4 if the level detection value is equal to or higher than the threshold value, and outputting a control signal so as to enable the measurement according to the frequency corresponding to the channel.

At the time of the detection of the signal level of each of the channels, the channel is preferably connected to the frequency measuring unit 4. The reason is that if the signal level is detected while an output end of the channel is left open, a value of a terminal impedance at the time of the detection and a value of a terminal impedance at the time of the measurement of the frequency by the frequency measuring unit 4 become different, which lowers accuracy of the detection of the signal level.

In this example, the frequency measuring unit 4 calculates a variation in frequency by digital processing based on a frequency signal corresponding to a difference between a frequency of the frequency signal from the oscillator circuit unit 10 and a frequency of a reference frequency signal, as will be described later, and different reference frequency signals need to be used depending on the oscillation frequencies of the used oscillator circuit units 10. Therefore, in this program, by finding a channel having the level detection value equal to or higher than the threshold value, it is possible to specify to which of bands of the band-pass filters 23a to 23c the frequency of the frequency signal corresponds. That is, the oscillation frequency of the oscillator circuit unit 10 connected to the instrument main body 20 is known. Therefore, the control signal for selecting the reference frequency corresponding to this frequency, for example, the control signal validating one of three reference frequency output units is output.

Next, the operation of the above-described embodiment will be described. First, upon power on of the instrument main body 20 side, the direct-current voltage is supplied to the internal circuit of the instrument main body 20 and at the same time, the direct-current voltage is supplied to the oscillator circuit unit 10 side via the coaxial cable 30 as previously described. It is assumed here that the oscillator circuit units 10 of three kinds, that is, one with 9 MHz, one with 30 MHz, and one with 60 MHz are usable, and the 9 MHz oscillator circuit unit 10 is currently connected to the instrument main body 20, and the 9 MHz quartz sensor 1 is inserted in this oscillator circuit unit 10. Then, in order to calculate a reference value, for instance, a solution not containing a substance to be sensed is injected into the quartz sensor 1, and the quartz resonator 24 is oscillated. This solution may be pure water or other solution.

Figure 5:
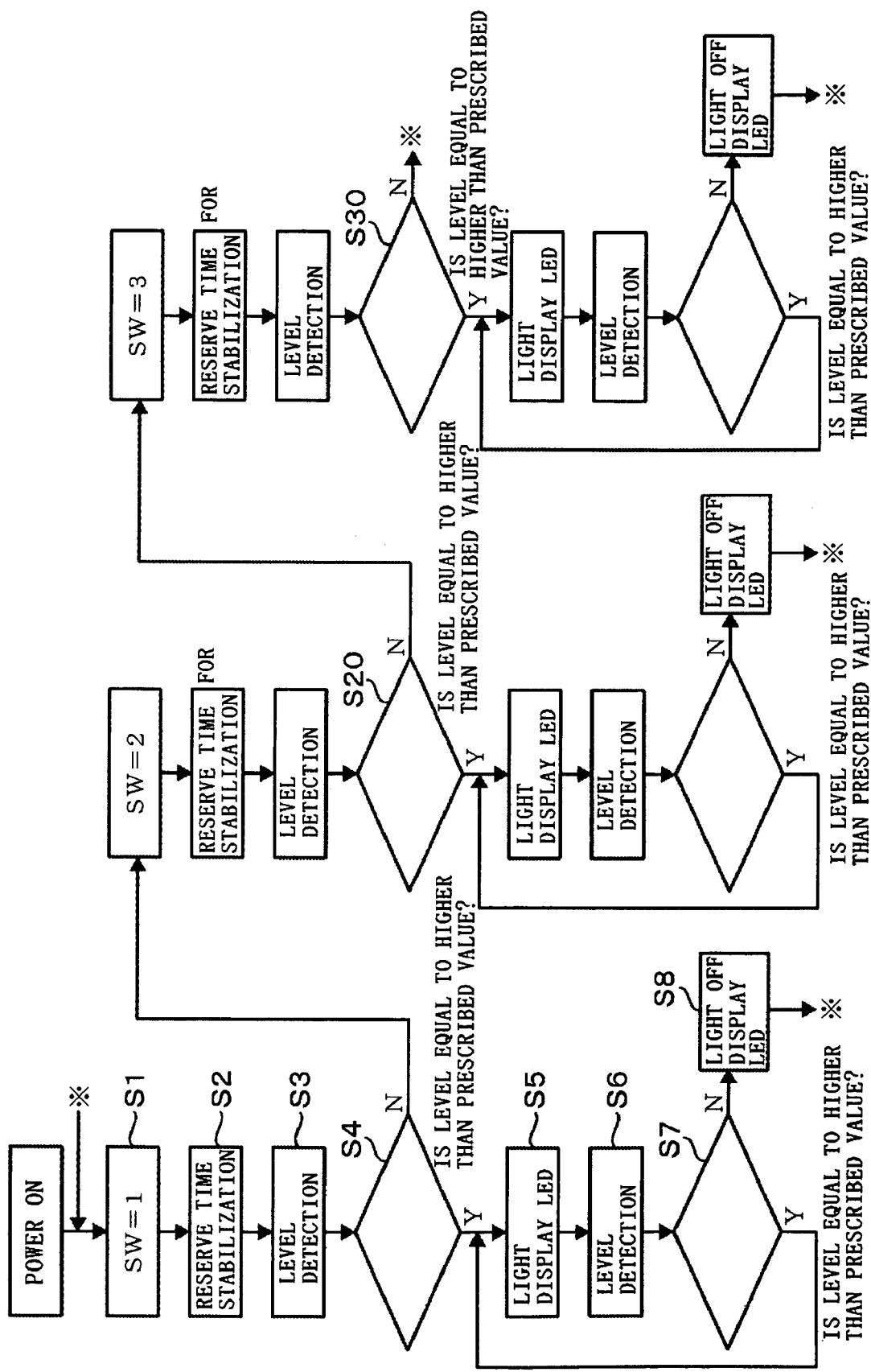
FIG. 5 is a flowchart showing part of the operation of the embodiment.

At this time, in the program 73, the steps proceed as shown in FIG. 5. Here, for convenience of description, the channel in which the 9 MHz band-pass filter 23a is provided is defined as a channel ch1, the channel in which the 30 MHz band-pass filter 23b is provided is defined as a channel ch2, and the channel in which the 60 MHz band-pass filter 23c is provided is defined as a channel ch3. First, the switching unit 5 selects the channel ch1 to connect the channel ch1 to the frequency measuring unit 4 (Step S1), and after the time required for the frequency signal of the channel ch1 to be stabilized, for example, one second passes (Step S2), the signal level of the channel ch1 is detected and it is determined whether not the signal level is equal to or higher than the threshold value (Steps S3 and S4). When the signal level is equal to or higher than the threshold value, the LED of the display unit 201 is lighted (Step S5). That is, in this case, it is known that the oscillation frequency of the oscillator circuit unit 10 is 9 MHz since the pass band of the band-pass filter 23a of the channel ch1 is 9 MHz, and therefore, a 10 MHz reference frequency which is a reference frequency used for the 9 MHz measurement in the frequency measuring unit 4 is selected for the frequency measurement. An example of this measurement will not be described in detail here in order to avoid the complication of the description.

After the completion of such frequency measurement, the result of the measurement, in this example, a frequency difference between the frequency of the frequency signal from the oscillator circuit unit 10 and the reference frequency is displayed on the display unit 201, and the lighted LED enables an operator to confirm the result. In the flow in FIG. 5, no description is given regarding the measurement, and therefore, after the display LED is lighted, the detection of the signal level of the channel ch1 and the determination regarding the signal level are performed again (Steps S6, S7), and when the level is equal to or higher than the threshold value, Steps S5 to S7 are repeated. When the quartz sensor 1 is detached after the end of the measurement, the control leaves Step 7 and returns to Step S1 after the display unit 201 is lighted off (Step S8).

On the other hand, when the signal level of the channel ch1 is lower than the threshold value, the switching unit 5 switches the channel ch1 to the channel ch2, and the same steps are performed. Specifically, when it is determined at Step 20 that the signal level of the channel ch2 is equal to or higher than the threshold value, it is known that the oscillation frequency of the oscillator circuit unit 10 is 30 MHz, and a 31 MHz reference frequency which is a reference frequency used for the 30 MHz measurement in the frequency measuring unit 4 is selected for the frequency measurement, and the result of the measurement is displayed on the display unit 201 in the same manner.

Further, when it is determined at Step 20 that the signal level of the channel ch2 is lower than the threshold value, the switching unit 5 switches the channel ch2 to the channel ch3, and the same steps are performed. Then, when it is determined at Step S30 that the signal level of the channel ch2 is lower than the threshold value, the control returns to Step S1. In this case, the signal levels of all of the 9 MHz, 30 MHz, 60 MHz frequency signals are lower than the threshold value, in other words, this implies that the quartz sensor 1 has some trouble. At this time, the display unit 201 is not lighted, which enables the operator to recognize that some abnormality is occurring. In this example, as a method of notifying a trouble, the method of keeping the display unit 201 lighted off is adopted, but it may be a method of displaying abnormality by lighting the display unit 201, a method of lighting an abnormality lamp, a method of sounding an abnormality buzzer, or the like.

After the frequency measurement is performed when a set amount of the solution not containing the substance to be sensed is put into the quartz sensor 1 as described above, a sample solution which is to undergo the measurement of a substance to be sensed is injected into the quartz sensor 1 containing the aforesaid solution, and the oscillation frequency of the quartz resonator of the quartz sensor 1 after the sample solution is put therein is found. For example, if the 9 MHz quartz sensor 1 is used, the frequency measurement proceeds while Steps S5 to S7 in FIG. 5 are repeated, and the frequency is displayed on the display unit 201. Then, a variation in the frequency after the sample solution is put is found, and the concentration of the substance to be sensed in the quartz sensor 1 is known by, for example, the use of a calibration curve, and as a result, the concentration of the substance to be sensed in the sample solution is known.

Figure 6:
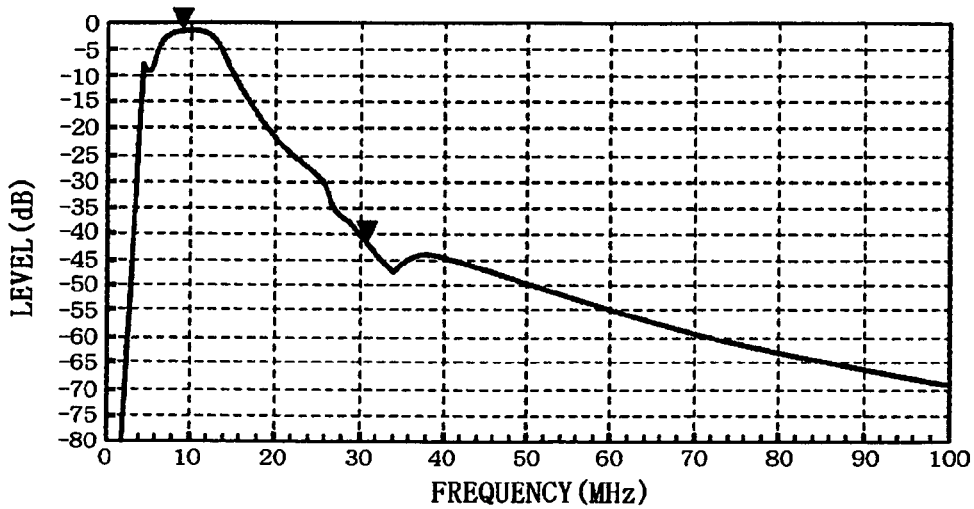
FIG. 6 is a characteristic chart showing a frequency pass characteristic of part of the circuit of the embodiment.
Figure 7:
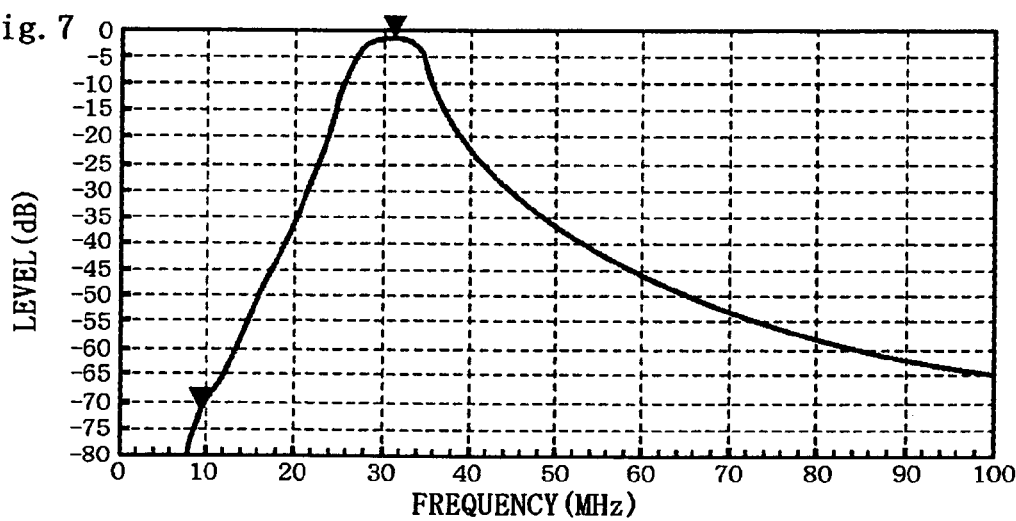
FIG. 7 is a characteristic chart showing a frequency pass characteristic of part of the circuit of the embodiment.
Figure 8:
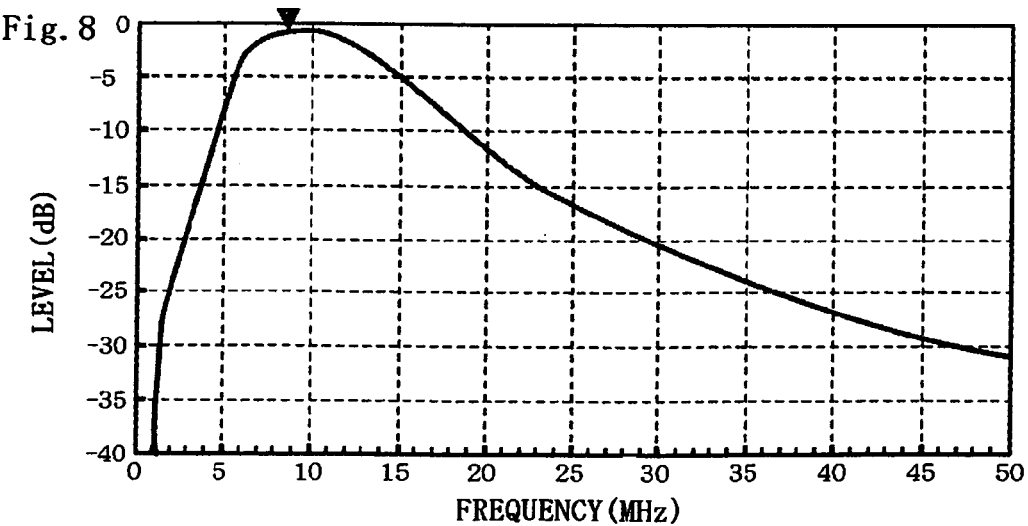
FIG. 8 is a characteristic chart showing a frequency pass characteristic of part of the circuit of the embodiment.

Here, FIG. 6 to FIG. 8 show the results of confirmed pass characteristics in the circuit. FIG. 6 corresponds to the result when the 9.2 MHz quartz sensor 1 is used in the circuit shown in FIG. 3, and shows a pass characteristic at the output end of the band-pass filter corresponding to this frequency in the frequency sorting unit 23. Further, FIG. 7 corresponds to the results when the 30.8 MHz quartz sensor 1 is used and similarly shows a pass characteristic at the output end of the corresponding band-pass filter. It is seen from the results that, when, for example, the 9.2 MHz oscillator circuit unit 10 and the 30.8 MHz oscillator circuit unit 10 are selectively used, a level difference in the both frequencies are sufficiently large at the output side of the frequency sorting unit 23, and therefore by setting the threshold value, it is possible to surely decide the magnitude of the signal level.

Further, FIG. 8 shows a pass characteristic at a branching point of the signal line and the power supply line 15 (the output side of the high-pass filter 14) in the 9.2 MHz oscillator circuit unit 10. It is seen from the result that the direct-current voltage supplied from the instrument main body 20 is supplied to the power supply line 15 side and an oscillation output does not enter the power supply line 15 side.

According to the embodiment described above, in adopting the structure in which the oscillator circuit unit 10 and the instrument body 20 are formed separately, a plurality of, three in this example, band-pass filters 23a to 23c having pass characteristics corresponding to the oscillation frequencies of the oscillator circuits 12 are provided in the instrument main body 20 side to sort the frequency signals, and the levels of the sorted frequency signals are detected. Therefore, it is possible to specify which of the channels (the band-pass filters 23a to 23c) has the signal level equal to or higher than the threshold value, based on the detection value of the signal level, and as a result, it is possible to know the oscillation frequency of the oscillator circuit unit 10. As a result, it is possible to control the switching unit so as to connect this channel to the measuring unit and to set the reference frequency used in the frequency measuring unit 4 to a value according to the oscillation output, which enables the frequency measurement. Therefore, it is possible to separately form the oscillator circuit unit 10 and the instrument main body 20 and select the oscillator circuit unit 10 with a proper frequency for the substance to be sensed, out of the plural kinds of frequencies, and in addition, to make the instrument main body 20 common to the oscillator circuit units 10.

Further, in the embodiment described above, the quartz sensor 1 whose quartz resonator is provided with the adsorption layer is used, but the present invention is also applicable to the quartz sensor 1 without the adsorption layer. For example, the present invention is also applicable to a case where it is examined how much amount of the adsorption layer, for example, some kind of antibody adheres to a surface of the electrode of the quartz resonator, for example, during a development stage or the research of the quartz sensor.

In the present invention, the structure of the instrument is not limited to the structure in which three kinds of the oscillator circuit units 10 are usable as described above, but may be a structure in which one selected from two kinds or four kinds or more of the oscillator circuit units 10 can be connected to the instrument main body 20. Further, the measurement by the frequency measuring unit 4 is not limited to the direct measurement of the frequency, but the frequency measuring unit 4 may detect a phase of the frequency signal and as a result detect the frequency.

Figure 9:
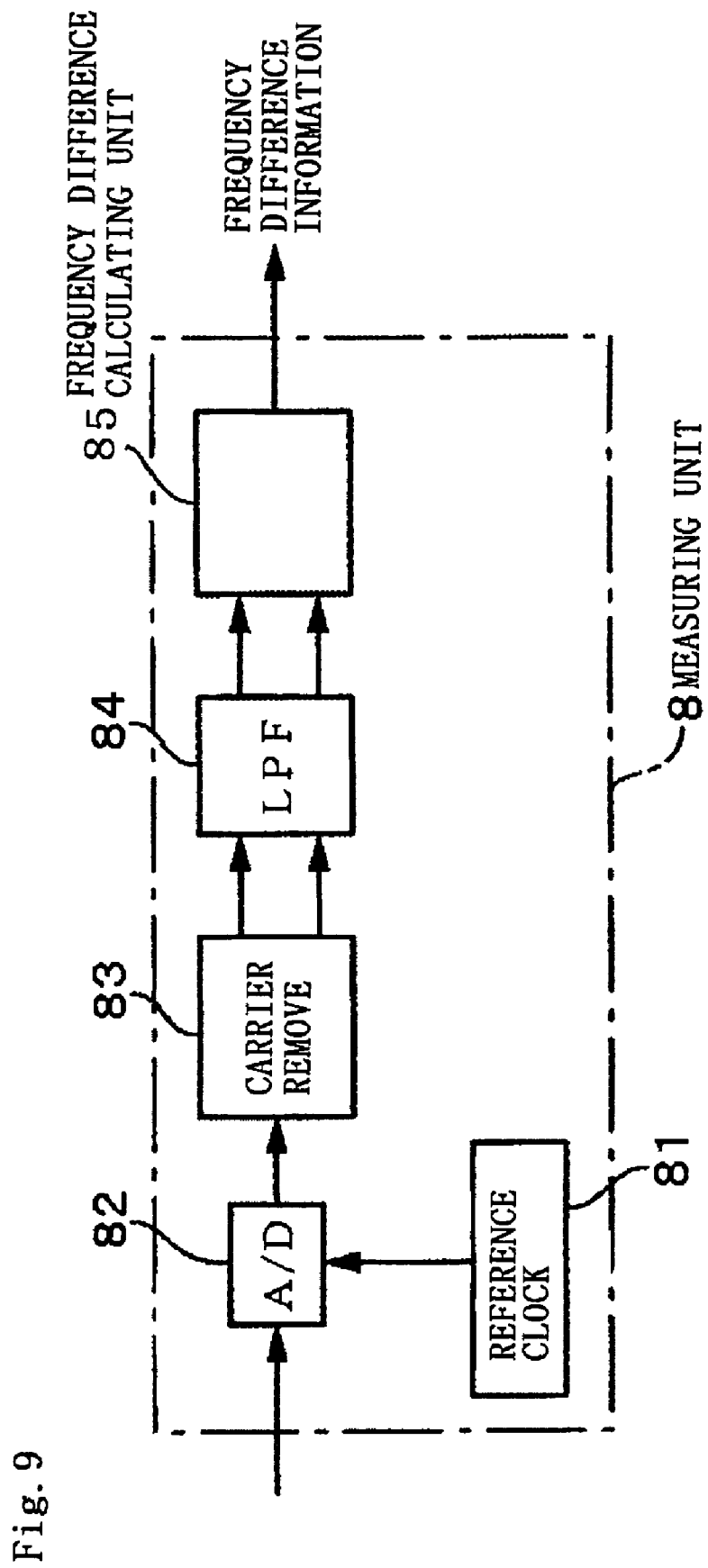
FIG. 9 is a block diagram showing an example of a measuring unit.

Here, an example of the frequency measuring unit 4 is shown in FIG. 9. In FIG. 9, 81 denotes a reference clock generating unit, and it outputs a clock signal, which is a frequency signal with extremely stable frequency, in order to sample the frequency signal from the switching unit 5. 82 denotes an A/D (analog/digital) converter, and it samples the frequency signal based on the clock signal from the reference clock generating unit 81 and outputs the sampling value as a digital signal. For example, when fc is 9 MHz, fs is set to 10 MHz, where fc is the frequency of the frequency signal and fs is the sampling frequency (frequency of the clock signal). In this case, a fundamental wave of the frequency signal specified by the output signal from the A/D converter 61 which is the digital signal is a 1 MHz sinusoidal wave. To be more specific, 9 MHz and 1 MHz mentioned here is 9.2 MHz and 0.8 MHz, but they are written as rough values for convenience sake.

On a subsequent stage of the A/D converter 82, a carrier remove 83 and a low-pass filter 84 are provided in this order. The carrier remove 83 and the low-pass filter 84 are used to extract a rotation vector which rotates at a frequency corresponding to a difference between, for example, the frequency of the 1 MHz sinusoidal signal specified by the digital signal from the A/D converter 82 and the frequency of a sinusoidal signal used for quadrature detection.

Figure 10:
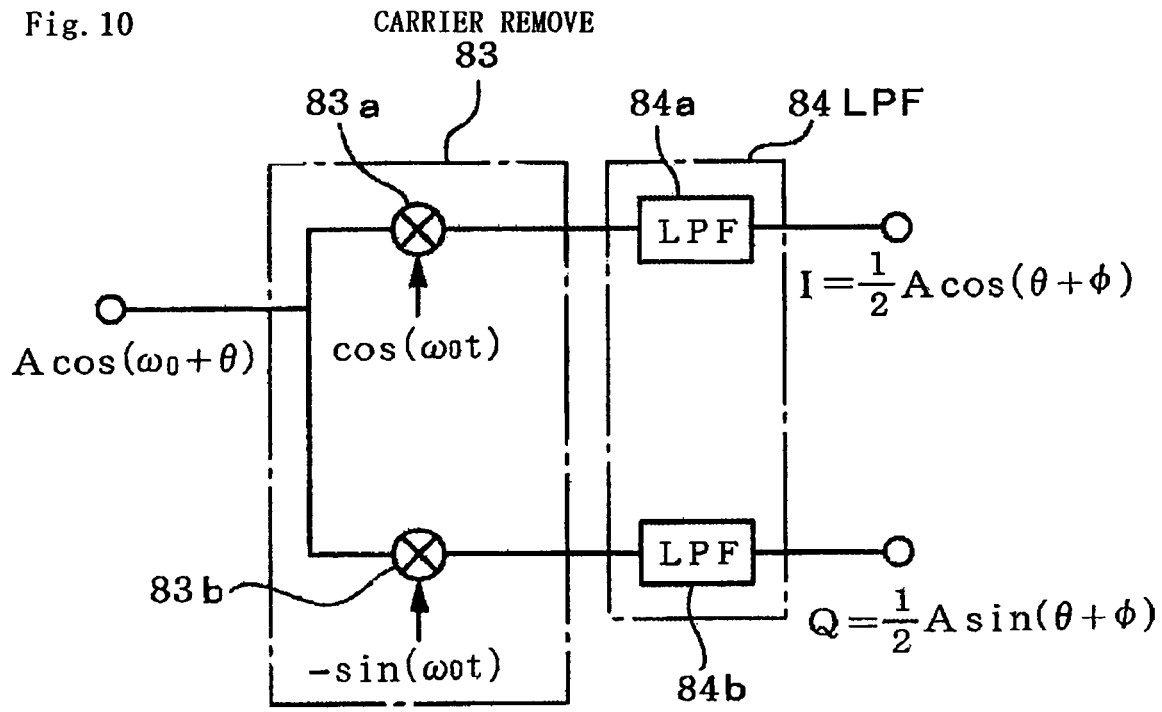
FIG. 10 is a block diagram showing part of the circuit block shown in FIG. 9.

For easier understanding of the operation of extracting the rotation vector, the sinusoidal signal specified by the digital signal from the A/D converter 82 is defined as A cos(ω0t+θ). As shown in FIG. 10, the carrier remove 83 includes a multiplying unit 83a multiplying the sinusoidal signal by cos (ω0t) and a multiplying unit 83b multiplying the sinusoidal signal by −sin(ω0t). That is, by such arithmetic operation, the quadrature detection is performed. An output of the multiplying unit 83a and an output of the multiplying unit 83b are expressed by an expression (2) and an expression (3) respectively.

$$A\cos(\omega 0t + \theta) \cdot \cos(\omega 0t) = \\ 1/2 \cdot A\cos\theta + 1/2\{\cos(2\omega 0t) \cdot \cos\theta + \sin(2\omega 0t) \cdot \sin\theta\} \quad (2)$$

$$A\cos(\omega 0t + \theta) \cdot -\sin(\omega 0t) = \\ 1/2 \cdot A\sin\theta - 1/2\{\sin(2\omega 0t) \cdot \cos\theta + \cos(2\omega 0t) \cdot \sin\theta\} \quad (3)$$

Therefore, when the output of the multiplying unit 83a and the output of the multiplying unit 83b are passed through low-pass filters 84a and 84b respectively, the 2ω0t frequency signal is filtered out, and as a result, ½·A cos θ and ½·A sin θ are extracted from the low-pass filter 84.

Then, when the frequency of the sinusoidal signal expressed as A cos(ω0t+θ) changes, A cos(ω0t+θ) becomes A cos(ω0t+θ+ω1t). Note that ω1 is sufficiently smaller than ω0. Therefore, ½·A cos θ becomes ½·A cos(θ+ω1t), and ½·A sin θ becomes ½·A sin(θ+ω1t). That is, the output obtained from the low-pass filter 84 is a signal corresponding to a variation ω1/2π of the frequency of the sinusoidal signal [A cos(ω0t+θ)]. That is, these values are a real part (I) and an imaginary part (Q) which are complex expression of the rotation vector rotating at the frequency corresponding to the difference between the frequency of the sinusoidal signal specified by the digital signal from the A/D converter 82 and the frequency ω0/2π of the sinusoidal signal used for the quadrature detection.

Figure 11:
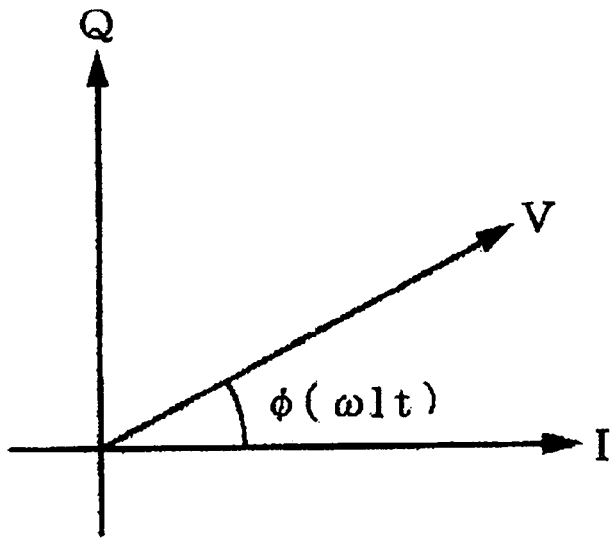
FIG. 11 is an explanatory chart showing a rotation vector extracted by the block diagram shown in FIG. 9.
Figure 12:
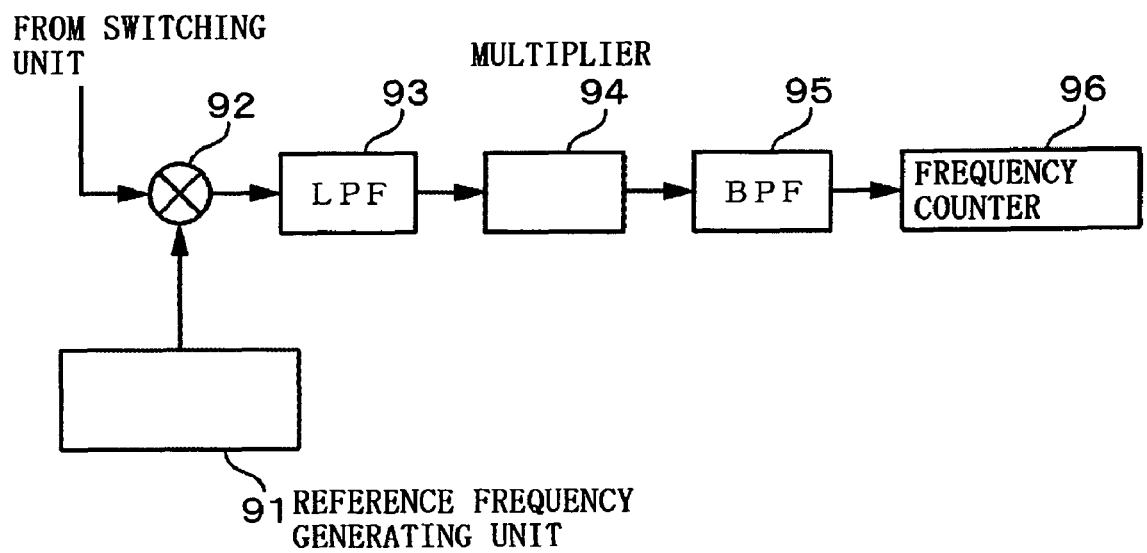
FIG. 12 is a block diagram showing another example of the measuring unit.

FIG. 11 is a chart showing this rotation vector and an angular velocity of this rotation vector is ω1. Therefore, if there is no change in the frequency of the sinusoidal signal, ω1t is zero and thus the rotation speed of the rotation vector is zero, but when due to the adsorption of the substance to be sensed by the quartz resonator 24, the frequency of the quartz resonator changes and accordingly the frequency of the sinusoidal signal changes, the rotation vector rotates at the rotation speed corresponding to the variation.

Incidentally, the angular velocity corresponding to the oscillation frequency of the quartz resonator in the absence of a substance to be sensed rarely agrees with the angular velocity of the sinusoidal signal used for the quadrature detection, and therefore, in actual practice, the angular velocity of the rotation vector corresponding to the oscillation frequency of the quartz resonator in the absence of the substance to be sensed and the angular velocity of the rotation vector corresponding to the oscillation frequency of the quartz resonator in the presence of the substance to be sensed are found, and a difference between the angular velocities is found. The difference between the angular velocities of the rotation vector is a value corresponding to the variation in the frequency of the quartz resonator caused by the adsorption of the substance to be sensed by the quartz resonator.

In the foregoing, the measuring unit is not limited to the structure performing the digital processing as described above, but as is described in the aforesaid patent document 2 and so on, it may be a circuit which extracts by a heterodyne detector 92 a frequency difference between the frequency of the frequency signal from the switching unit, for example, 9 MHz, and the reference frequency of the reference frequency signal of the reference frequency generating unit 91, for example, 10 MHz, and measures the frequency of the frequency signal corresponding to the frequency difference.

The invention claimed is:

1. A sensing instrument which uses a sensing sensor including a piezoelectric resonator changing in natural frequency by the adsorption of a sample and which senses the adsorption of the sample based on the change in the natural frequency of the piezoelectric resonator, the instrument comprising:

an oscillator circuit unit to which the sensing sensor is connected and which includes an oscillator circuit for oscillating the piezoelectric resonator of the sensing sensor;

an instrument main body attachably/detachably connected to the oscillator circuit unit and including a measuring unit measuring a signal regarding a frequency of an oscillation output of the oscillator circuit;

a frequency sorting circuit provided in the instrument main body, and including a plurality of channels and a plurality of band-pass filters, the channels branching off from a frequency signal line extending from the oscillator circuit unit, and the band-pass filters being provided in the channels respectively and having pass characteristics corresponding to the oscillation frequencies of the oscillator circuits respectively;

a switching unit connecting a selected channel among the plural channels to the measuring unit;

a plurality of level detecting circuits detecting signal levels at output sides of the plural band-pass filters respectively; and a control unit comparing level detection values, which are detected by the plural level detecting circuits respectively, with a threshold value, controlling the switching unit so as to connect, to the measuring unit, a channel for which the level detection value equal to or higher than the threshold value is output, and controlling the measuring unit according to a frequency of a frequency signal corresponding to the connected channel.

2. The sensing instrument according to claim 1, wherein the piezoelectric resonator includes: an electrode provided on a front surface of a piezoelectric piece; and an adsorption layer formed on a front surface of the electrode to adsorb a substance to be sensed, and changes in the natural frequency when the substance to be sensed is adsorbed.

3. The sensing instrument according to claim 1, wherein the measuring unit extracts a difference between a reference frequency selected from a plurality of reference frequencies and the frequency of the frequency signal from the oscillator circuit and measures a signal regarding the frequency difference, and the control unit selects the reference frequency from the plural reference frequencies according to the frequency of the frequency signal corresponding to the channel for which the level detection value equal to or higher than the threshold value is output.

4. The sensing instrument according to claim 1, wherein at the time of the detection of the signal levels at the output sides of the band-pass filters, the control unit controls the switching unit so as to connect the channel whose signal level is to be detected to the measuring unit.

5. The sensing instrument according to claim 1, wherein the oscillator circuit unit and the instrument main body are attachably/detachably connected via a cable.

6. The sensing instrument according to claim 1, wherein:
- a feed line feeding a direct-current voltage to the frequency signal line on an input side of the frequency sorting circuit is connected to the instrument main body;
- a power supply line for taking out the direct-current voltage to an output side of the oscillator circuit is connected to the oscillator circuit unit;
- low-pass filters blocking passage of the oscillation output are provided in the feed line and the power supply line respectively;
- filters blocking passage of the direct-current voltage are provided between a connection point of the feed line and the band-pass filters in the frequency signal line, and between a connection point of the power supply line and the oscillator circuit in the frequency signal line respectively; and
- the direct-current voltage of the instrument main body side is supplied to the oscillator circuit side via the frequency signal line.

* * * * *